(12) United States Patent
Looi et al.

(10) Patent No.: US 11,911,059 B2
(45) Date of Patent: Feb. 27, 2024

(54) SURGICAL SHUNT ASSEMBLY TOOL

(71) Applicant: THE HOSPITAL FOR SICK CHILDREN, Toronto (CA)

(72) Inventors: Thomas Looi, Markham (CA); Grace Yee Yan Lai, Toronto (CA); Brian E. William Hanak, IV, Loma Linda, CA (US); Pascal Voyer-Nguyen, Montreal (CA); James Drake, Toronto (CA)

(73) Assignee: THE HOSPITAL FOR SICK CHILDREN, Toronto (CA)

( * ) Notice: Subject to any disclaimer, the term of this patent is extended or adjusted under 35 U.S.C. 154(b) by 0 days.

(21) Appl. No.: 17/236,246

(22) Filed: Apr. 21, 2021

(65) Prior Publication Data

US 2021/0322041 A1 Oct. 21, 2021

Related U.S. Application Data

(60) Provisional application No. 63/013,037, filed on Apr. 21, 2020.

(51) Int. Cl.
*A61B 17/28* (2006.01)
*A61B 17/29* (2006.01)
*A61M 27/00* (2006.01)

(52) U.S. Cl.
CPC ......... *A61B 17/282* (2013.01); *A61M 27/002* (2013.01); *A61B 2017/2829* (2013.01); *A61B 2017/2931* (2013.01); *A61M 2209/04* (2013.01)

(58) Field of Classification Search
CPC .......... A61B 17/282; A61B 2017/2829; A61B 2017/2931; A61M 27/002; A61M 2209/04; A61M 27/006
See application file for complete search history.

(56) References Cited

U.S. PATENT DOCUMENTS 5,188,638 A * 2/1993 Tzakis ............... A61B 17/1152
227/176.1
5,391,181 A * 2/1995 Johnson ............... A61B 17/282
81/424.5

(Continued)

*Primary Examiner* — Kathleen S Holwerda
*Assistant Examiner* — Serenity A Miller
(74) *Attorney, Agent, or Firm* — HILL & SCHUMACHER

(57) ABSTRACT

The present disclosure provides a surgical shunt assembly tool that provides a more efficacious grip on the catheter tubes and prevent the tip of the catheter from buckling while the catheter is pushed onto the tip of the valve during installation of shunts during CSF shunt surgery. The tool includes standard handles such as used in a shodded mosquito tool having a clamping jaw integrated into the distal end section of the handle. The distal jaw includes two forcep jaw sections each having a proximal end integrally formed with a distal end of a distal end arm section of one of the two handle arms, and a distal end section extending away from the distal end arm section. The distal end sections of the forcep jaw sections are cylindrically shaped such that when the forcep jaw is closed by bringing the two forcep jaw sections together, a cylinder is formed having a diameter substantially equal to a diameter of a catheter tube to be attached to a shunt valve tip. The proximal ends of the forcep jaw sections are oval shaped and have a size such that when the forcep jaw is closed bringing the two forcep jaw sections together, an oval shaped opening is formed having a size smaller than the diameter of the catheter tube such that the catheter tube is squeezed closed to provide a firm grip of the tool of the catheter tube.

9 Claims, 9 Drawing Sheets

(56) References Cited

U.S. PATENT DOCUMENTS

| | | | | |
|---|---|---|---|---|
| 5,591,203 A * | 1/1997 | Fahy | .................. | A61B 17/11 |
| | | | | 606/151 |
| 2005/0004590 A1* | 1/2005 | Waters | ................ | A61B 17/282 |
| | | | | 606/170 |
| 2006/0030880 A1* | 2/2006 | Tylke | ................ | A61B 17/2812 |
| | | | | 606/205 |
| 2008/0177297 A1* | 7/2008 | Steiner | ................ | A61B 17/282 |
| | | | | 606/205 |
| 2012/0059407 A1* | 3/2012 | Isch | .................... | A61B 17/282 |
| | | | | 606/205 |
| 2015/0100080 A1* | 4/2015 | Kohler | ................ | A61B 17/282 |
| | | | | 606/205 |
| 2016/0331408 A1* | 11/2016 | Benson | .............. | A61B 17/4241 |
| 2019/0142425 A1* | 5/2019 | Smith | .................... | A61B 17/10 |
| | | | | 606/205 |
| 2020/0229832 A1* | 7/2020 | Recanati | ............ | A61B 17/4241 |

\* cited by examiner

SURGICAL SHUNT ASSEMBLY TOOL

FIELD

The present disclosure relates to a surgical shunt assembly tool for aiding in installing cerebrospinal fluid (CSF) shunts in patients.

BACKGROUND

Infection remains a common and devastating complication of cerebrospinal fluid (CSF) shunts, with reported rates ranging from 6 to 15%[16] and reinfection after treatment of first infection in up to 16% of patients[17]. Risk factors include young age at time of surgery in infants[8,13,16], previous neurosurgery[16], shunt surgery following external ventricular drainage[6], postoperative CSF leak[8], shunt revision within prior 90 days[14], gastrostomy tube[1,16], and surgeon experience[10,16]. Kulkarni, et al[8] also demonstrated that following pediatric CSF shunt surgery, 33.4% of surgical team members had at least one hole in their "sterile" surgical gloves and defects in surgical gloves was associated with a large number of infections. Protocols involving double gloving[5,10,19,20] and changing gloves prior to handling the hardware[2,5,10,12] have been employed with subsequent reduction in infection rates. Many protocols also support a "no-touch" technique while handling shunt components[3,5,10,16].

No-touch technique stipulates that shunt equipment be manipulated with sterile instruments rather than with gloved hands. However, in our experience with current instruments available, "no-touch" has proven difficult in many cases, involving multiple attempts and often resorting to hand manipulation with antibiotic soaked gauze. As one can imagine, this approach has practical limitations that makes the task of applying catheter tubing to shunt valves challenging. The gauze creates bulk that makes it hard to visualize the catheter and valve, diminishes tactile feedback, and limits the ability to working in a small surgical corridor.

Many clinical protocols for CSF shunt surgery have adapted "no-touch" techniques in the attempt to reduce shunt infections[3,5,10,11]. Mosquito forceps with rubber shods over the tips are most often used for connection of shunt catheters to valves. However, the forceps do not provide a good grip on the catheter and it is often difficult to attach the two parts, especially when the valve is already in place under the skin, as per standard practice[18]. Surgeons often resort to using their gloved hands, and if able, attempt to manipulate the shunt components with anti-biotic soaked gauze.

Thus it would be very advantageous to provide a surgical shunt assembly tool that provides a more efficacious grip on the catheter tubes and prevent the tip of the catheter from buckling while the catheter is pushed onto the tip of the valve during installation of shunts during CSF shunt surgery.

SUMMARY

In light of shortcomings inherent in the current practice of the well-accepted "no-touch" surgical technique for catheter connection, the present inventors have conceived of and designed a new surgical instrument specifically engineered to assist in connecting CSF shunt catheter tubing to shunt valves and connectors.

Thus the present disclosure provides a surgical shunt tool for installing cerebrospinal fluid (CSF) shunts in patients. The surgical shunt assembly tool provides a more efficacious grip on the catheter tubes and prevent the tip of the catheter from buckling while the catheter is pushed onto the tip of the valve during installation of shunts during CSF shunt surgery. The tool includes standard handles such as used in a shodded mosquito tool having a clamping jaw integrated into the distal end section of the handle. The distal jaw includes two forcep jaw sections each having a proximal end integrally formed with a distal end of a distal end arm section of one of the two handle arms, and a distal end section extending away from the distal end arm section. The distal end sections of the forcep jaw sections are cylindrically shaped such that when the forcep jaw is closed by bringing the two forcep jaw sections together, a cylinder is formed having a diameter substantially equal to a diameter of a catheter tube to be attached to a shunt valve tip. The proximal ends of the forcep jaw sections are oval shaped and have a size such that when the forcep jaw is closed bringing the two forcep jaw sections together, an oval shaped opening is formed having a size smaller than the diameter of the catheter tube such that the catheter tube is squeezed closed to provide a firm grip of the tool of the catheter tube.

An embodiment of the surgical shunt assembly tool comprises a handle having first and second elongate arms with a proximal end of each of the two elongate arms configured to be gripped by a digit of a clinician.

A distal end of the handle is integrally formed with forcep jaws, and the forcep jaws include a first forcep jaw section integrally formed at a proximal end thereof to an end of a distal end arm section of the first elongate arm and a second forcep jaw section integrally formed at a proximal end of an end of a distal end arm section of the second elongate arm. The first and second elongate arms being pivotally connected to each other at a location spaced from the forcep jaws.

Each of the forcep jaw sections have a proximal end integrally formed with a distal end of the distal end arm section and a distal end section extending away from the distal end arm section. The distal end section of the forcep jaw sections are cylindrical in shape such that when the forcep jaw is closed, a cylinder is formed having a diameter substantially equal to a diameter of a catheter tube to be attached to a shunt valve tip. The proximal ends of the forcep jaw sections are oval shaped and having a size such that when the forcep jaw is closed an oval shaped opening is formed having a size smaller than said diameter of the catheter tube such that the catheter tube is squeezed closed to provide a firm grip of the tool of the catheter tube.

The distal end sections of each arm attached to its associated forcep jaw section may be at pre-selected angle with respect to the first and second elongate arms. The pre-selected angle may be in a range from about 0 degrees to about 90 degrees.

Each elongate arm, its associated distal end arm section and associated forcep jaw section may be formed as an integrally formed unitary single piece.

Alternatively, each elongate arm, its associated distal end arm section and associated forcep jaw section may be formed as two separate pieces configured to be temporarily mated to each other, in which each distal end arm section and associated forcep jaw section are formed as an integrally formed unitary single piece, and a distal end of each arm section is configured to temporarily mate to an associated distal arm section which is integrally attached to its associated forcep jaw section.

A further understanding of the functional and advantageous aspects of the disclosure can be realized by reference to the following detailed description and drawings.

BRIEF DESCRIPTION OF THE DRAWINGS

Preferred embodiments of the disclosure will now be described, by way of example only, with reference to the drawings, in which.

DETAILED DESCRIPTION OF THE DISCLOSURE

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

Some of the Figures may not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present disclosure. For purposes of teaching and not limitation, the illustrated embodiments are directed to a surgical shunt assembly tool for aiding in installing cerebrospinal fluid (CSF) shunts in patients.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Figure 1A:
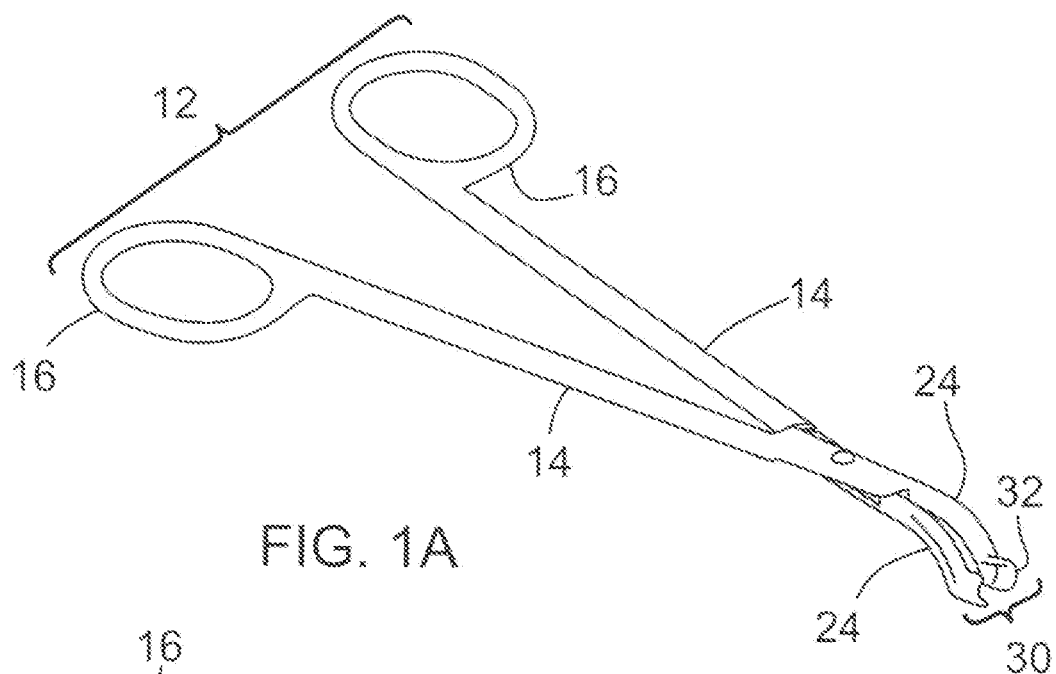
FIG. 1A is a perspective view of the surgical shunt assembly tool constructed in accordance with the present disclosure in the open position.
Figure 1B:
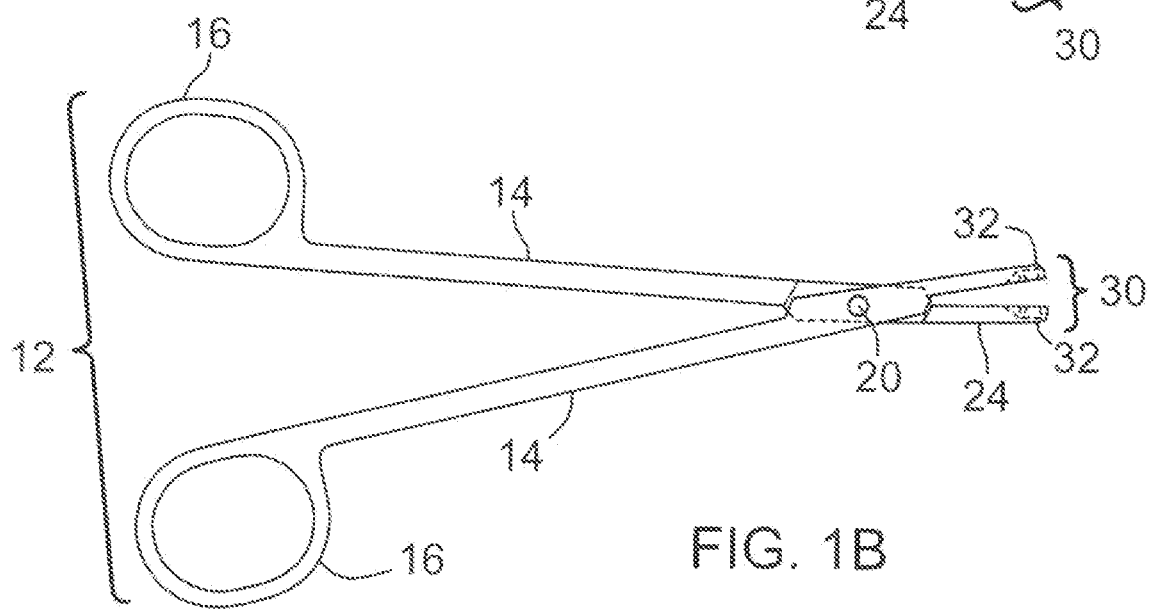
FIG. 1B is a plan view of the surgical shunt assembly tool of FIG. 1A in the open position.

Referring to FIGS. 1A to 1B, a surgical shunt assembly tool for aiding in installing cerebrospinal fluid (CSF) shunts in patients constructed in accordance with the present disclosure is shown generally at 10. Tool 10 includes a handle section 12 which includes elongate arms 14 and generally circular loops 16 at the proximal ends of arms 14 with loops 16 being sized and shaped to receive digits of a clinician's hand. The distal end of handle section 12 is integrally formed with forcep jaws 30, specifically the forcep jaws 30 include a first forcep jaw section 32 integrally formed at its proximal end to the first elongate arm 14 and a second forcep jaw section 32 is integrally formed its proximal end to the second elongate arm 14. As best seen in FIG. 1A, the end distal end sections 24 of arms 14 have an arcuate shape. The two elongate arms 14 are pivotally connected to each other at a pivot connection 20 at a location spaced from the forcep jaws 30 just before arms 14 assume the arcuate shape in arm sections 24.

It will be appreciated that while the distal ends of arms 14 are shown to be arcuate in distal end sections 24, it will be appreciated that the angle of the bends of section 24 relative to the rest of arms 14 may be at any angle, depending on the preferences and dexterity of the clinician using the forcep tool 10. Thus, the angle of distal end sections 24 relative to the rest of arms 14 may be in a range from about 0 degrees to 90 degrees. To this end, the present tool 10 may be configured to have a standard handle such as those having the same size and design as mosquito forceps, but configured to take interchangeable jaws 30 that can be rapidly attached to the distal end of the arms 14 of the handle 12.

Figure 1C:
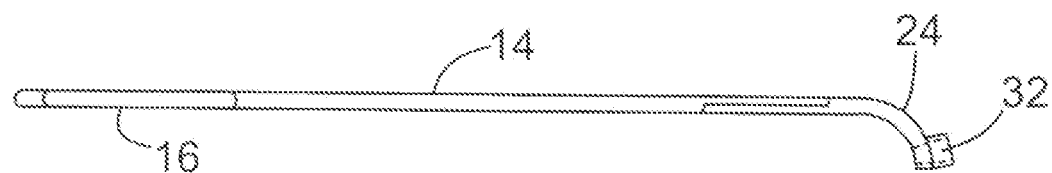
FIG. 1C is a side view of the surgical shunt assembly tool of FIG. 1A in the open position.
Figure 2A:
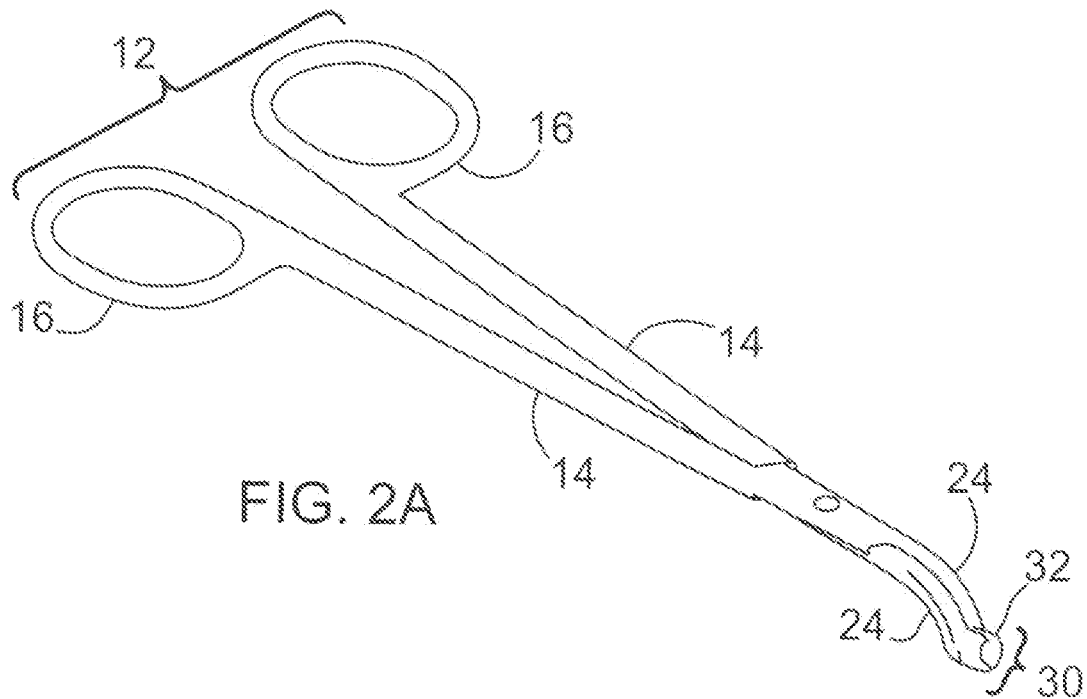
FIG. 2A is a perspective view of the surgical shunt assembly tool constructed in accordance with the present disclosure in the closed position.
Figure 2B:
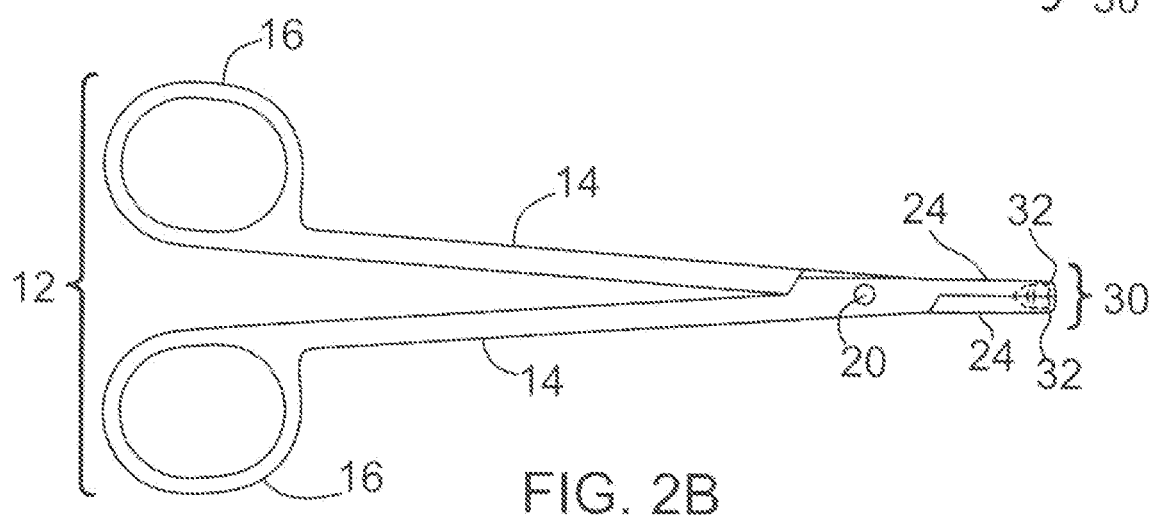
FIG. 2B is a plan view of the surgical shunt assembly tool of FIG. 2A in the closed position.
Figure 2C:
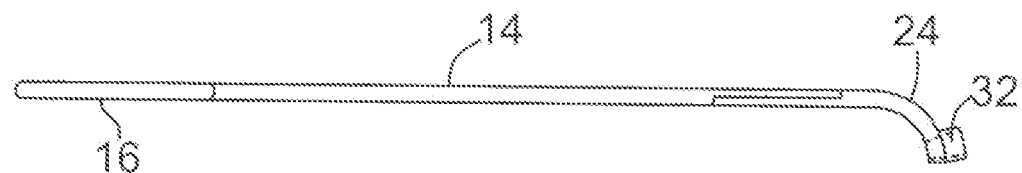
FIG. 2C is a side view of the surgical shunt assembly tool of FIG. 2A in the closed position.
Figure 6A:
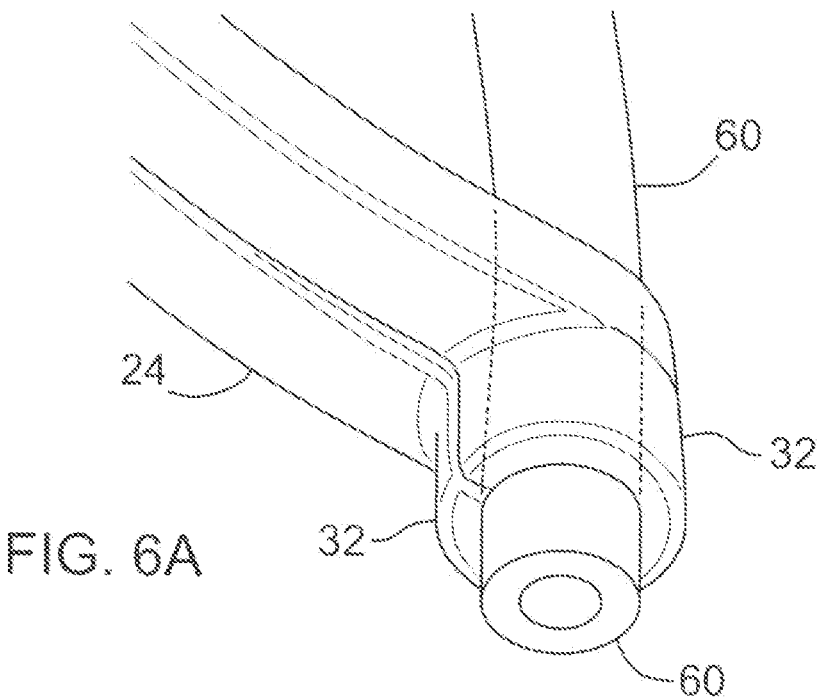
FIG. 6A is a perspective view of the distal end of the present shunt assembly tool with the jaws closed and gripping a catheter tube showing the front open end of the catheter tube ready to be attached to a shunt.
Figure 6B:
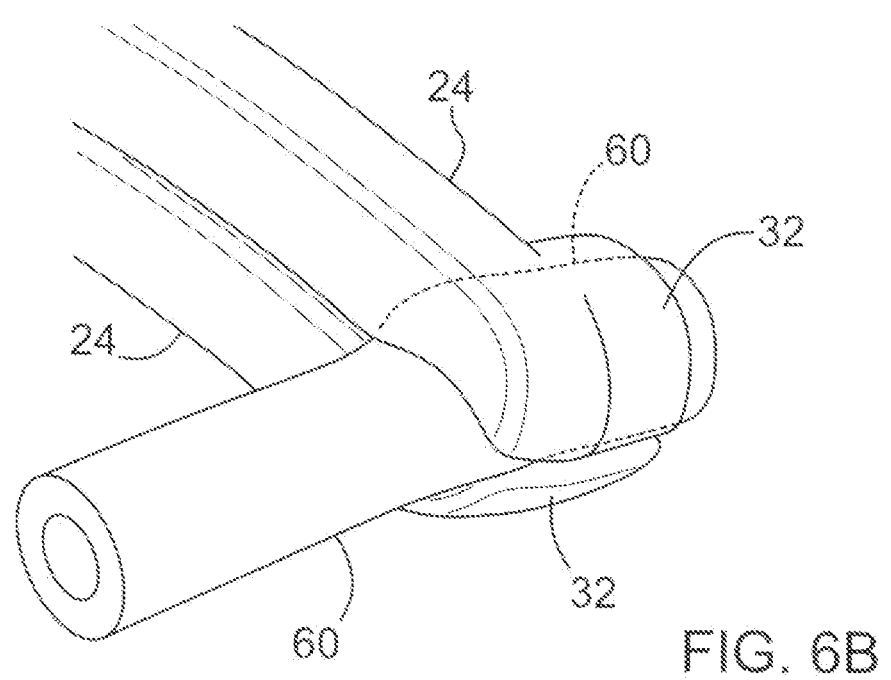
FIG. 6B is similar to FIG. 6A looking from the back of the closed jaws showing the catheter tube being squeezed and gripped by the jaws.

FIGS. 2A to 2C are similar to FIGS. 1A to 1C but show the tool 10 closed with arms 14 squeezed together as they would be when a catheter tube 60 is being held by the jaws 30, as in FIGS. 6A and 6B.

Figure 3A:
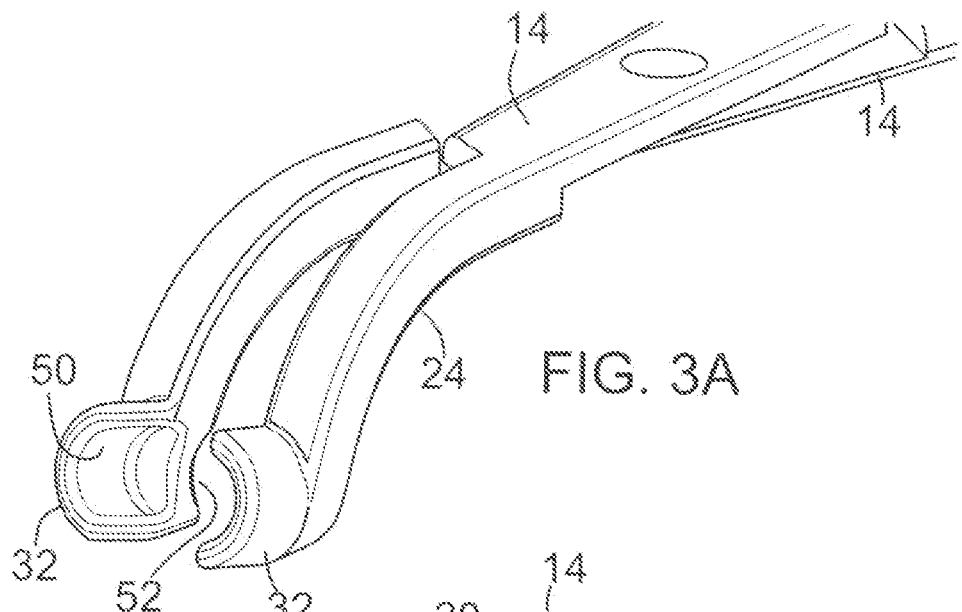
FIG. 3A is a partial perspective view of the tool showing distal end of the surgical shunt assembly in the open position, which is an enlargement of the distal end of the tool in FIG. 1A.
Figure 3B:
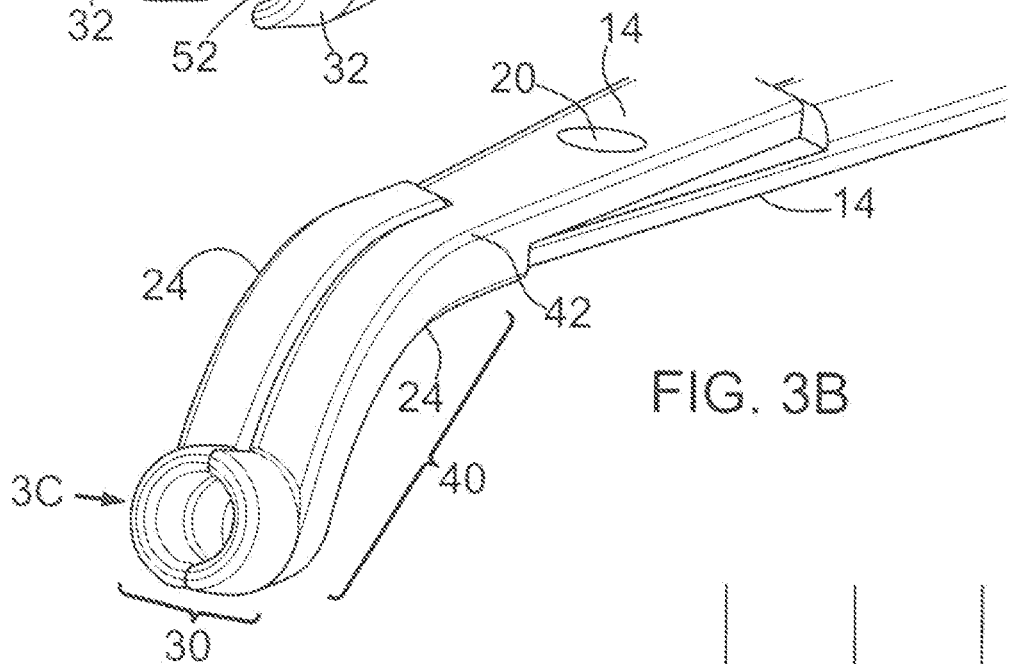
FIG. 3B is a partial perspective view of the tool showing distal end of the surgical shunt assembly in the closed position, which is an enlargement of the distal end of the tool in FIG. 2A.

FIG. 3A shows the partial perspective enlarged view from FIG. 1A of the tool 10 showing distal end with the jaws 30 in the open position while FIG. 3B shows the jaws 30 closed. Referring again to FIG. 3A, the jaw sections 32 have a jaw section 52 which is coplanar with are sections 24 and also each have a jaw section 50 projecting from arm sections 24 with sections 50 having a cylindrical cross section so that when the forcep jaw 30 is closed, these projecting jaw sections 50 define a cylinder having a circular cross section sized to accept standard, commercially available polydimethylsiolxane shunt catheter tubing 60 as shown in FIGS. 6A and 6B such that the outer diameter of the tubing 60 is substantially same as the inner diameter of this cylindrical section of the closed jaw 30.

Figure 3C:
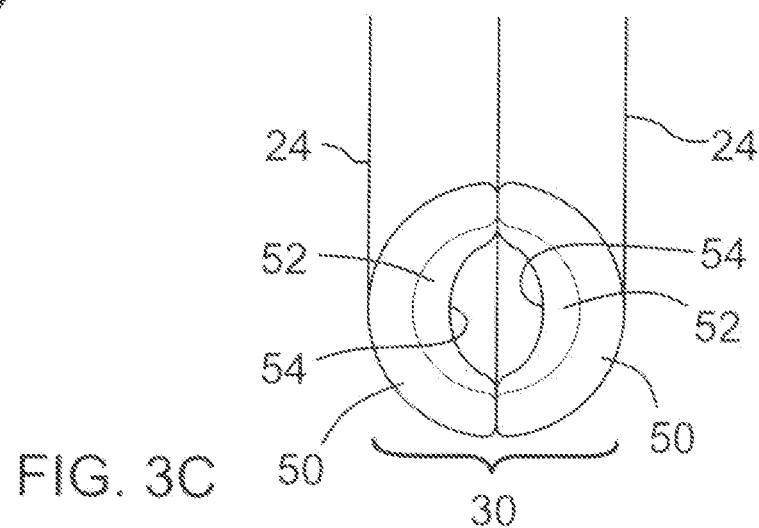
FIG. 3C is a view along arrow 3C in FIG. 3B showing a top view looking down through the closed jaw.

Referring to FIG. 3C, the jaw sections 32 also configured so that jaw sections 52 coplanar with arm sections 24 are not cylindrical but rather tapered so that when jaw 30 is closed, the two tapered jaw sections 52 define an opening 54 with an oval cross section much smaller than the diameter of tubing 60 thereby squeezing the tubing together to provide grip and friction to prevent the catheter tube 60 from slipping distally when being applied to the shunt valve. All edges are smooth to prevent damage to the catheter tube 60. The clinician can then hood the open cylindrical part of the end of hose 60 over the plastic male connector tip of the valve (not shown) and prevent buckling of the catheter 60 as it is pushed into position.

Figure 4A:
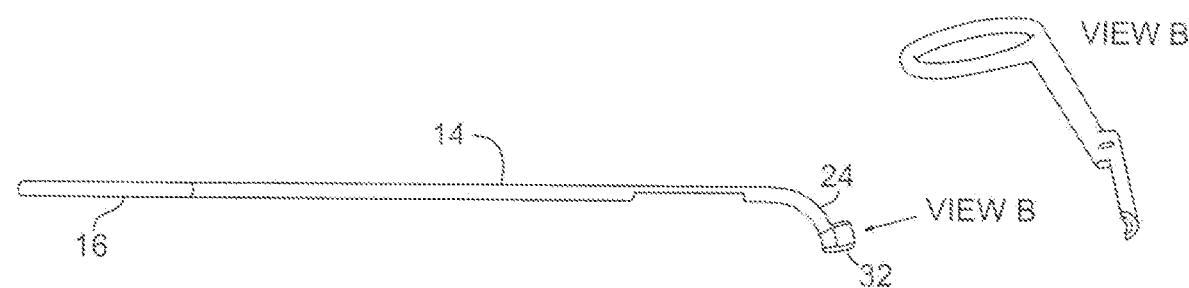
FIG. 4A is a medial view of the side of one of the arms with auxiliary view B showing the arm seen looking down into the distal end of the jaw section.
Figure 4B:
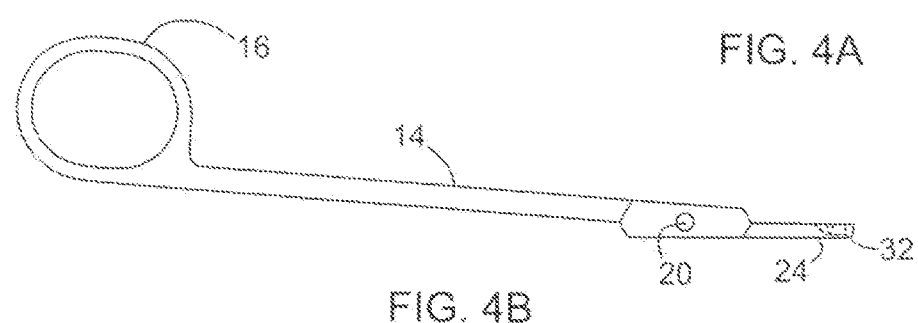
FIG. 4B is a plan view of one of the arms.
Figure 4C:
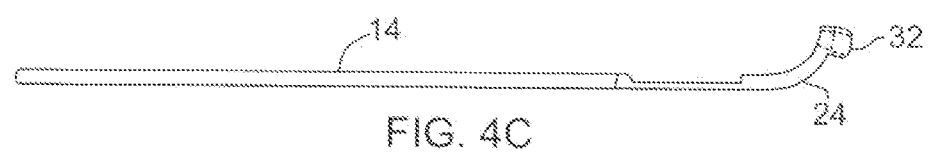
FIG. 4C is a lateral view of the side of one of the arms.
Figure 5A:
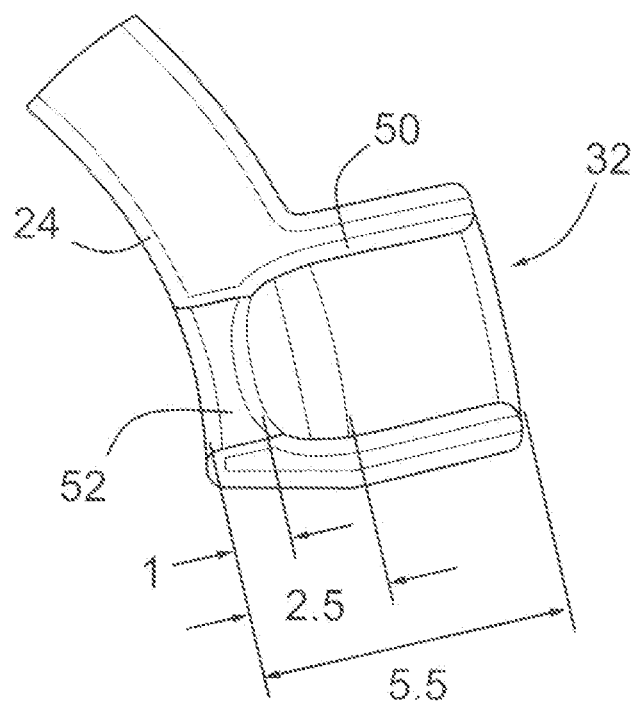
FIG. 5A is an expanded view of Detail A in FIG. 4A showing a medial side view showing distal end of one of two jaw sections.
Figure 5B:
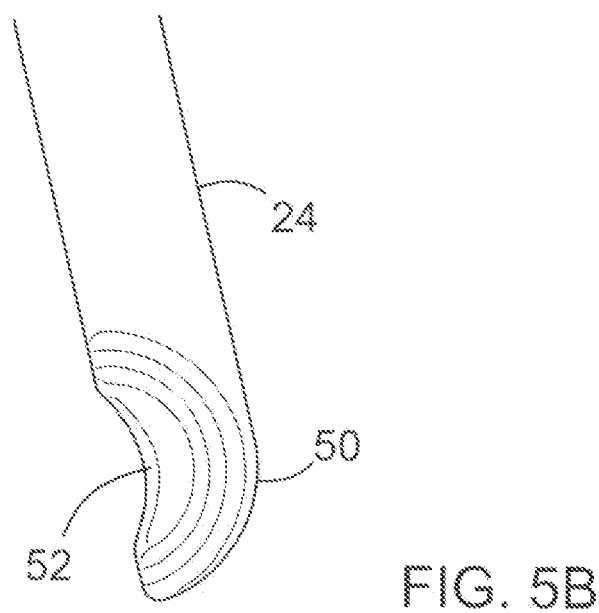
FIG. 5B is an expanded view of Detail C in FIG. 4A showing a top view looking down onto the distal end of the jaw section.

Further details of the structure in which the section 50 of jaw section 32 projecting out from its associate arm section 24 are seen in FIG. 5A, which is an expanded view of Detail A in FIG. 4A. FIG. 5B is an expanded view of Detail C in FIG. 4A showing a top view looking down onto the distal end of the jaw section showing the jaw section 52 which is substantially coplanar with the arm section 24 and is tapered so that when jaws 30 are closed an oval opening with a size much smaller than tube 60 is produced, again shown in FIG. 6B.

The dimensions given in FIGS. 5A and 5B are designed for a 3.0 mm diameter catheter but it will appreciated this is only exemplary and the jaw sizes can be scaled as require for use with larger and smaller diameter catheters. If using a larger diameter catheter, the tool can be palmed and not completely closed. If using a smaller diameter, the tapered distal end will still hold the catheter tight and prevent slipping distally when pushing the catheter tubing 60 into position. When the catheter tube 60 is grasped such that the distal end of the tool 10 is at a location along the catheter tube 60 that is about 2-3 mm longer than the length of the valve tip, the catheter tube 60 can be placed in one movement without the need to reposition the tool further back to push the catheter to the end of the tip.

The shunt assembly tool 10 may be constructed so that each arm 14, 24 and associated jaw section 32 are made as a single integral unitary piece as shown in FIGS. 1A to 3C. Alternatively, referring to FIG. 3B, the angled arm sections 24 and associated jaw sections 32 may be integrally formed as one piece 40 which are then attached to a standard pair of mosquito forceps at or around the position marked by 42 using standard quick connect mechanisms such as clips or as a sleeve, in a similar manner to rubber shods currently used for such forceps. Different end pieces 40 can then be made with a range of different angles to provide choices for the clinician to select the end pieces 40 best suited to his or hers ergonometric requirements.

Figure 7A:
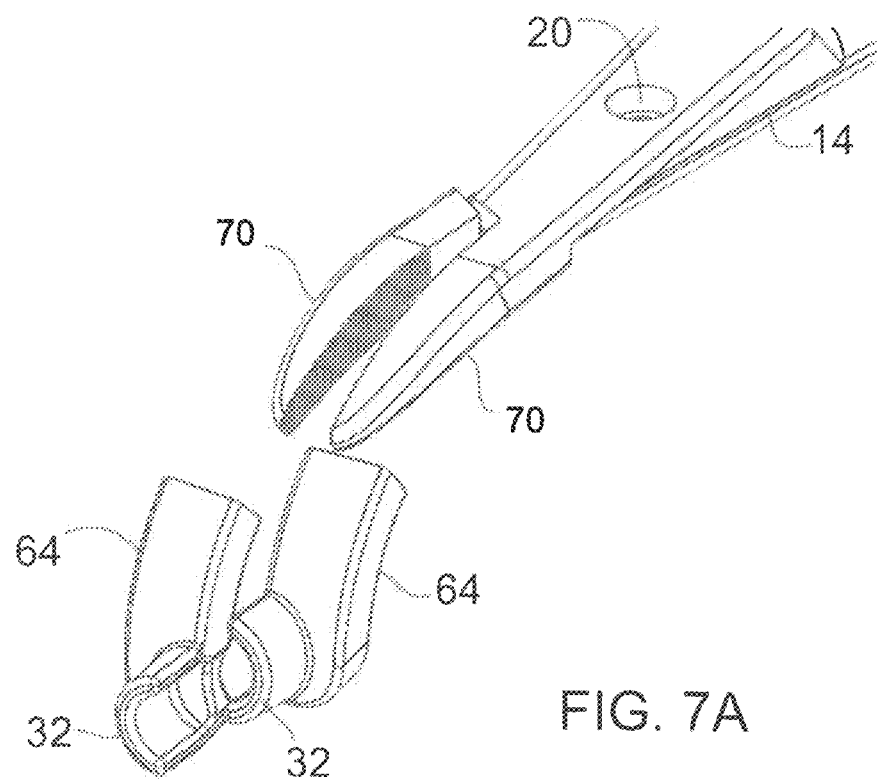
FIG. 7A shows a front disassembled perspective view of the distal ends of an embodiment of a shunt assembly tool in which the distal arm sections and jaws are integrally formed and separate from the distal ends of the handle arms of the tool and configured so that the jaws can be quickly connected to the distal ends of the handle arms.
Figure 7B:
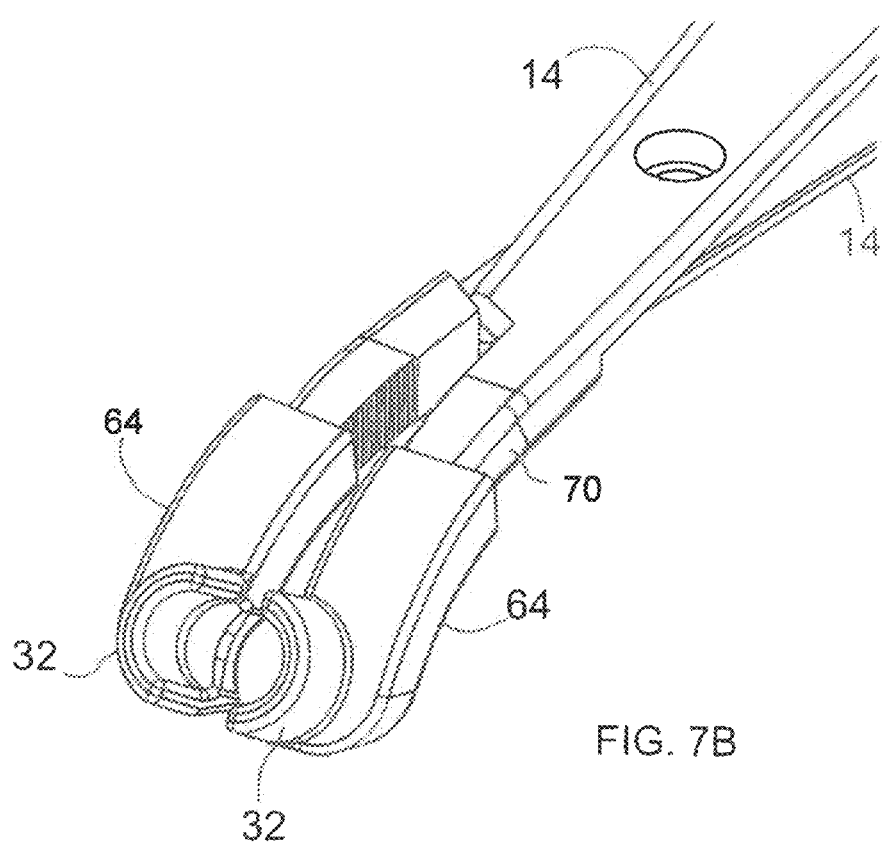
FIG. 7B is similar to FIG. 7A but showing the separate distal end and jaw sections partially assembled.
Figure 7C:
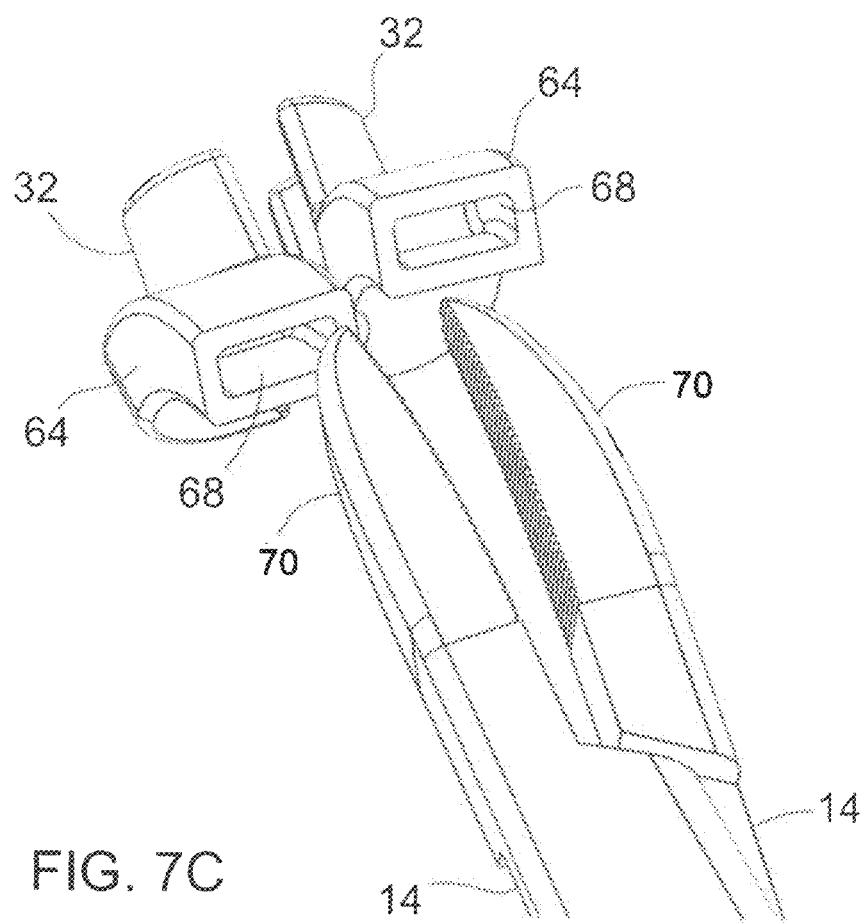
FIG. 7C is similar to FIG. 7A but now taken from the back showing the jaw and distal arm end sections separate from the distal ends of the arms of the handle section.

A non-limiting exemplary embodiment of a tool with interchangeable jaws is shown in FIGS. 7A, 7B and 7C. This embodiment of the jaw tool includes arm sections 64 at which the distal ends have jaw sections 32 (identical to those in FIGS. 1 to 6) integrally formed as one piece with arm sections 64. As seem from FIG. 7C, arm sections 64 include passageways 68. The distal ends of arms 14 terminate in latching members 70 which have a size and shape to be received into passageways 68 in arm sections 64. The handles including arm sections 14 and distal arm sections of latching members 70 may represent an existing tool (e.g., surgical clamps and the like) where the cerrated surfaces on the inner sides of distal sections of latching members 70 serve to improve grip on tissues when used without the jaw 30 attached thereto. Thus, the arm sections 64 to which the jaw sections 32 are standard and the arm sections 64 are configured to be able to attach the jaws 30 onto a variety of instruments to be used for the purpose described.

CONCLUSIONS

Given the morbidity and cost associated with CSF shunt infections, many surgical protocols have been implemented to minimize infection. The "no-touch" technique for intraoperative handling of shunt hardware is widely adopted but often difficult given the lack of a surgical tool specifically designed for the task of connecting the shunt catheter to the shunt valve. The surgical shunt assembly tool disclosed herein for this purpose has demonstrated safety, ease of use, and reduced time and number of attempts required for this task. The implementation of this tool provides a cost-effective and simple solution to improve adherence to the "no-touch" technique, make application of catheter tubing to shunt valves more straightforward and expeditious, and allow components to be connected in a smaller working space.

The foregoing description of the preferred embodiments of the disclosure has been presented to illustrate the principles of the disclosure and not to limit the disclosure to the particular embodiment illustrated. It is intended that the scope of the disclosure be defined by all of the embodiments encompassed within the following claims and their equivalents.

REFERENCES

1. Al-Holou W N, Wilson T J, Ali Z S, Brennan R P, Bridges K J, Guivatchian T, et al: Gastrostomy tube placement increases the risk of ventriculoperitoneal shunt infection: a multiinstitutional study. J Neurosurg:1-6, 2018
2. Bashir A, Sorensen P: Evaluation of intraoperative glove change in prevention of postoperative cerebrospinal fluid shunt infections, and the predictors of shunt infection. Br J Neurosurg 31:452-458, 2017

3. Faillace W J: A no-touch technique protocol to diminish cerebrospinal fluid shunt infection. Surg Neurol 43:344-350, 1995
4. Hayashi T, Shirane R, Yokosawa M, Kimiwada T, Tominaga T: Efficacy of intraoperative irrigation with saline for preventing shunt infection. J Neurosurg Pediatr 6:273-276, 2010
5. Hommelstad J, Madso A, Eide P K: Significant reduction of shunt infection rate in children below 1 year of age after implementation of a perioperative protocol. Acta Neurochir (Wien) 155:523-531, 2013
6. Kestle J R, Riva-Cambrin J, Wellons J C, 3rd, Kulkarni A V, Whitehead W E, Walker M L, et al: A standardized protocol to reduce cerebrospinal fluid shunt infection: the Hydrocephalus Clinical Research Network Quality Improvement Initiative. J Neurosurg Pediatr 8:22-29, 2011
7. Krause M, Mahr C V, Schob S, Nestler U, Wachowiak R: Topical instillation of vancomycin lowers the rate of CSF shunt infections in children. Childs Nerv Syst 35:1155-1157, 2019
8. Kulkarni A V, Drake J M, Lamberti-Pasculli M: Cerebrospinal fluid shunt infection: a prospective study of risk factors. J Neurosurg 94:195-201, 2001
9. Mallucci C L, Jenkinson M D, Conroy E J, Hartley J C, Brown M, Dalton J, et al: Antibiotic or silver versus standard ventriculoperitoneal shunts (BASICS): a multicentre, single-blinded, randomised trial and economic evaluation. Lancet 394:1530-1539, 2019
10. Omrani O, O'Connor J, Hartley J, James G: Effect of introduction of a standardised peri-operative protocol on CSF shunt infection rate: a single-centre cohort study of 809 procedures. Childs Nerv Syst 34:2407-2414, 2018
11. Pirotte B J, Lubansu A, Bruneau M, Loqa C, Van Cutsem N, Brotchi J: Sterile surgical technique for shunt placement reduces the shunt infection rate in children: preliminary analysis of a prospective protocol in 115 consecutive procedures. Childs Nerv Syst 23:1251-1261, 2007
12. Rehman A U, Rehman T U, Bashir H H, Gupta V: A simple method to reduce infection of ventriculoperitoneal shunts. J Neurosurg Pediatr 5:569-572, 2010
13. Riva-Cambrin J, Kestle J R, Holubkov R, Butler J, Kulkarni A V, Drake J, et al: Risk factors for shunt malfunction in pediatric hydrocephalus: a multicenter prospective cohort study. J Neurosurg Pediatr 17:382-390, 2016
14. Rogers E A, Kimia A, Madsen J R, Nigrovic L E, Neuman M I: Predictors of ventricular shunt infection among children presenting to a pediatric emergency department. Pediatr Emerg Care 28:405-409, 2012
15. Sarmey N, Kshettry V R, Shriver M F, Habboub G, Machado A G, Weil R J: Evidence-based interventions to reduce shunt infections: a systematic review. Childs Nerv Syst 31:541-549, 2015
16. Simon T D, Butler J, Whitlock K B, Browd S R, Holubkov R, Kestle J R, et al: Risk factors for first cerebrospinal fluid shunt infection: findings from a multi-center prospective cohort study. J Pediatr 164:1462-1468 e1462, 2014
17. Simon T D, Kronman M P, Whitlock K B, Gove N E, Mayer-Hamblett N, Browd S R, et al: Reinfection after treatment of first cerebrospinal fluid shunt infection: a prospective observational cohort study. J Neurosurg Pediatr 21:346-358, 2018
18. Tamer W A E, A.: Ventriculoperitoneal Shunt, in Nader R G, C.; Berta, S. C. I; Sabbagh, A. J.; Levy, M. L. (ed): Neurosurgery Tricks of the Trade: Cranial, ed 1st: Thieme, 2013
19. Tulipan N, Cleves M A: Effect of an intraoperative double-gloving strategy on the incidence of cerebrospinal fluid shunt infection. J Neurosurg 104:5-8, 2006
20. Yang M M H, Hader W, Bullivant K, Brindle M, Riva-Cambrin J: Calgary Shunt Protocol, an adaptation of the Hydrocephalus Clinical Research Network shunt protocol, reduces shunt infections in children. J Neurosurg Pediatr:1-9, 2019

Therefore what is claimed is:

1. A surgical shunt assembly tool for attaching a catheter tube to a shunt valve tip, the catheter tube having an outer diameter, comprising: a handle having first and second elongate arms with a proximal end of each of said first and second elongate arms configured to be gripped by a digit of a clinician; a forcep including a first forcep law section attached to a distal end section of each of the first and second elongate arms, said first and second elongate arms being pivotally connected to each other at a location spaced from said distal end section of each of said first and second elongate arms; and each first forcep jaw section having a second forcep jaw section integrally formed therewith, the first forcep jaw sections having a size and shape that define an oval shaped opening when the forcep is closed, each second forcep jaw section having a size and shape that forms a cylinder with a circular shaped opening when the forcep is closed, said circular shaped opening having a diameter greater than the oval shaped opening when the forcep is closed, the oval shaped opening and the circular shaped opening being colinear, the diameter of the circular shaped opening being equal to the outer diameter of the catheter tube to be attached to a shunt valve tip and a size of the oval shaped opening selected to pinch closed the catheter tube when the forcep is closed.

2. The tool according to claim 1, wherein the distal end sections of each arm attached to its associated first forcep jaw section is at a pre-selected angle with respect to said first and second elongate arms.

3. The tool according to claim 2, wherein said pre-selected angle is in a range from about 0 degrees to about 90 degrees.

4. The tool according to claim 3, wherein each elongate arm, its associated distal end section and associated first forcep jaw section are formed as an integrally formed unitary single piece.

5. The tool according to claim 3, wherein each elongate arm, its associated distal end section and associated first forcep jaw section are formed as two separate pieces configured to be temporarily mated to each other, in which each first forcep jaw section is integrally formed with a sleeve section as a unitary single piece, and wherein a distal end of each arm is configured to temporarily mate to and be received in said sleeve section.

6. The tool according to claim 2, wherein each elongate arm, its associated distal end section and associated first forcep jaw section are formed as an integrally formed unitary single piece.

7. The tool according to claim 2, wherein each elongate arm, its associated distal end section and associated first forcep jaw section are formed as two separate pieces configured to be temporarily mated to each other, in which each first forcep jaw section is integrally formed with a sleeve section as a unitary single piece, and wherein a distal end of each arm is configured to temporarily mate to and be received in said sleeve section.

8. The tool according to claim 1, wherein each elongate arm, its associated distal end section and associated first forcep jaw section are formed as an integrally formed unitary single piece.

9. The tool according to claim 1, wherein each elongate arm, its associated distal end section and associated first forcep jaw section are formed as two separate pieces configured to be temporarily mated to each other, in which each first forcep jaw section is integrally formed with a sleeve section as a unitary single piece, and wherein a distal end of each arm is configured to temporarily mate to and be received in said sleeve section.

* * * * *

UNITED STATES PATENT AND TRADEMARK OFFICE
CERTIFICATE OF CORRECTION

PATENT NO. : 11,911,059 B2
APPLICATION NO. : 17/236246
DATED : February 27, 2024
INVENTOR(S) : Thomas Looi et al.

It is certified that error appears in the above-identified patent and that said Letters Patent is hereby corrected as shown below:

In the Claims

Column 8, Lines 14-37, Please amend Claim 1 as indicated:
1. A surgical shunt assembly tool for attaching a catheter tube to a shunt valve tip, the catheter tube having an outer diameter, comprising: a handle having first and second elongate arms with a proximal end of each of said first and second elongate arms configured to be gripped by a digit of a clinician; a forcep including a first forcep jaw section attached to a distal end section of each of the first and second elongate arms, said first and second elongate arms being pivotally connected to each other at a location spaced from said distal end section of each of said first and second elongate arms; and each first forcep jaw section having a second forcep jaw section integrally formed therewith, the first forcep jaw sections having a size and shape that define an oval shaped opening when the forcep is closed, each second forcep jaw section having a size and shape that forms a cylinder with a circular shaped opening when the forcep is closed, said circular shaped opening having a diameter greater than the oval shaped opening when the forcep is closed, the oval shaped opening and the circular shaped opening being colinear, the diameter of the circular shaped opening being equal to the outer diameter of the catheter tube to be attached to a shunt valve tip and a size of the oval shaped opening selected to pinch closed the catheter tube when the forcep is closed.

Signed and Sealed this
Thirteenth Day of August, 2024

Katherine Kelly Vidal
*Director of the United States Patent and Trademark Office*